United States Patent

Kado

(10) Patent No.: US 11,036,025 B2
(45) Date of Patent: Jun. 15, 2021

(54) MEDICAL OBSERVATION APPARATUS AND MEDICAL OBSERVATION SYSTEM

(71) Applicant: Sony Olympus Medical Solutions Inc., Tokyo (JP)

(72) Inventor: Masataka Kado, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/789,429

(22) Filed: Feb. 13, 2020

(65) Prior Publication Data

US 2020/0310078 A1    Oct. 1, 2020

(30) Foreign Application Priority Data

Mar. 25, 2019    (JP) .............. JP2019-057312

(51) Int. Cl.
| | |
|---|---|
| *G02B 7/02* | (2021.01) |
| *H04N 5/232* | (2006.01) |
| *H04N 5/225* | (2006.01) |
| *A61B 90/20* | (2016.01) |
| *G02B 7/28* | (2021.01) |
| *G02B 7/09* | (2021.01) |
| *G02B 1/02* | (2006.01) |
| *G02B 21/36* | (2006.01) |
| *G02B 21/02* | (2006.01) |

(52) U.S. Cl.
CPC .............. *G02B 7/028* (2013.01); *A61B 90/20* (2016.02); *G02B 7/09* (2013.01); *G02B 7/28* (2013.01); *G02B 21/025* (2013.01); *G02B 21/361* (2013.01); *H04N 5/2253* (2013.01); *H04N 5/2254* (2013.01); *H04N 5/23212* (2013.01)

(58) Field of Classification Search
None
See application file for complete search history.

(56) References Cited

U.S. PATENT DOCUMENTS

| | | | |
|---|---|---|---|
| 2006/0036162 A1* | 2/2006 | Shahidi | A61B 34/20 600/424 |
| 2014/0093228 A1* | 4/2014 | Gredegard | G03B 3/04 396/97 |
| 2017/0066131 A1* | 3/2017 | Kamikawa | B25J 9/1697 |
| 2017/0109889 A1* | 4/2017 | Yun | H04N 5/232125 |
| 2017/0176704 A1* | 6/2017 | Hirose | A61B 90/25 |

FOREIGN PATENT DOCUMENTS

JP    2000-075213 A    3/2000

* cited by examiner

*Primary Examiner* — Rebecca A Volentine
(74) *Attorney, Agent, or Firm* — Xsensus LLP

(57) ABSTRACT

A medical observation apparatus includes: an optical structure including at least one lens; an image sensor configured to capture an image formed by the optical structure; a temperature sensor configured to detect an environmental temperature of the optical structure; and circuitry configured to generate temperature information based on a detection result of the temperature sensor, and calculate a second focal length obtained by correcting a first focal length based on the temperature information and the first focal length calculated based on a lens position.

8 Claims, 6 Drawing Sheets

| ENVIRON-MENTAL TEMPERATURE | ACTUAL FOCAL LENGTH [mm] | WD OUTPUT VALUE IN CASE OF NOT PERFORMING CORRECTION | CORRECTION VALUE [mm] | WD OUTPUT VALUE AFTER PERFORMING CORRECTION BASED ON TEMPERATURE |
|---|---|---|---|---|
| 10°C | 490 | WD500 | -10 | WD490 |
| 25°C | 500 | WD500 | 0 | WD500 |
| 40°C | 510 | WD500 | +10 | WD510 |

|  | CORRECTION VALUE [mm] | | |
| --- | --- | --- | --- |
|  | 10 TO 20°C | 20 TO 30°C | 30 TO 40°C |
| WD200 TO 400 | -5 | ±0 | +5 |
| WD400 TO 600 | -10 | ±0 | +10 |

MEDICAL OBSERVATION APPARATUS AND MEDICAL OBSERVATION SYSTEM

This application claims priority from Japanese Application No. 2019-057312, filed on Mar. 25, 2019, the contents of which are incorporated by reference herein in its entirety.

BACKGROUND

The present disclosure relates to a medical observation apparatus and a medical observation system.

In the related art, as a medical observation system for observing a minute part of a brain, heart, or the like of a patient who is an object to be observed when performing an operation on the minute part, an optical microscope system including a plurality of arm units, a support unit which implements movement with a total of 6 degrees of freedom, that is, 3 degrees of freedom of translation and 3 degrees of freedom of rotation, and a microscope unit which is provided at a distal end of the support unit and includes a magnifying optical system or an image sensor which magnifies the minute part has been known.

In recent years, when performing an operation using a microscope system, a navigation apparatus which detects an observation position of a microscope unit and a position of a treatment tool, and displays the observation position and the like on a preoperative image has been employed as auxiliary means for performing a more accurate operation (see, for example, JP 2000-75213 A). In a case of the navigation apparatus, for example, three or more light emitting diodes are attached to the microscope unit, positions thereof are measured by a charge-coupled device (CCD) camera, and an observation position is calculated in consideration of a focal length of an optical system of the microscope unit.

Further, in some microscope systems, information on image capturing of a focal length and the like at a current position of the microscope unit may be displayed.

SUMMARY

In the optical system included in the microscope unit, characteristics of a lens may change due to a change in environmental temperature during use and the like, and a focal length may change even at the same lens position. If the focal length changes, a focal length based on a lens position does not match an actual focal length, such that accurate information may not be obtained.

According to one aspect of the present disclosure, there is provided a medical observation apparatus including: an optical structure including at least one lens; an image sensor configured to capture an image formed by the optical structure; a temperature sensor configured to detect an environmental temperature of the optical structure; and circuitry configured to generate temperature information based on a detection result of the temperature sensor, and calculate a second focal length obtained by correcting a first focal length based on the temperature information and the first focal length calculated based on a lens position.

DETAILED DESCRIPTION

Figure 1:
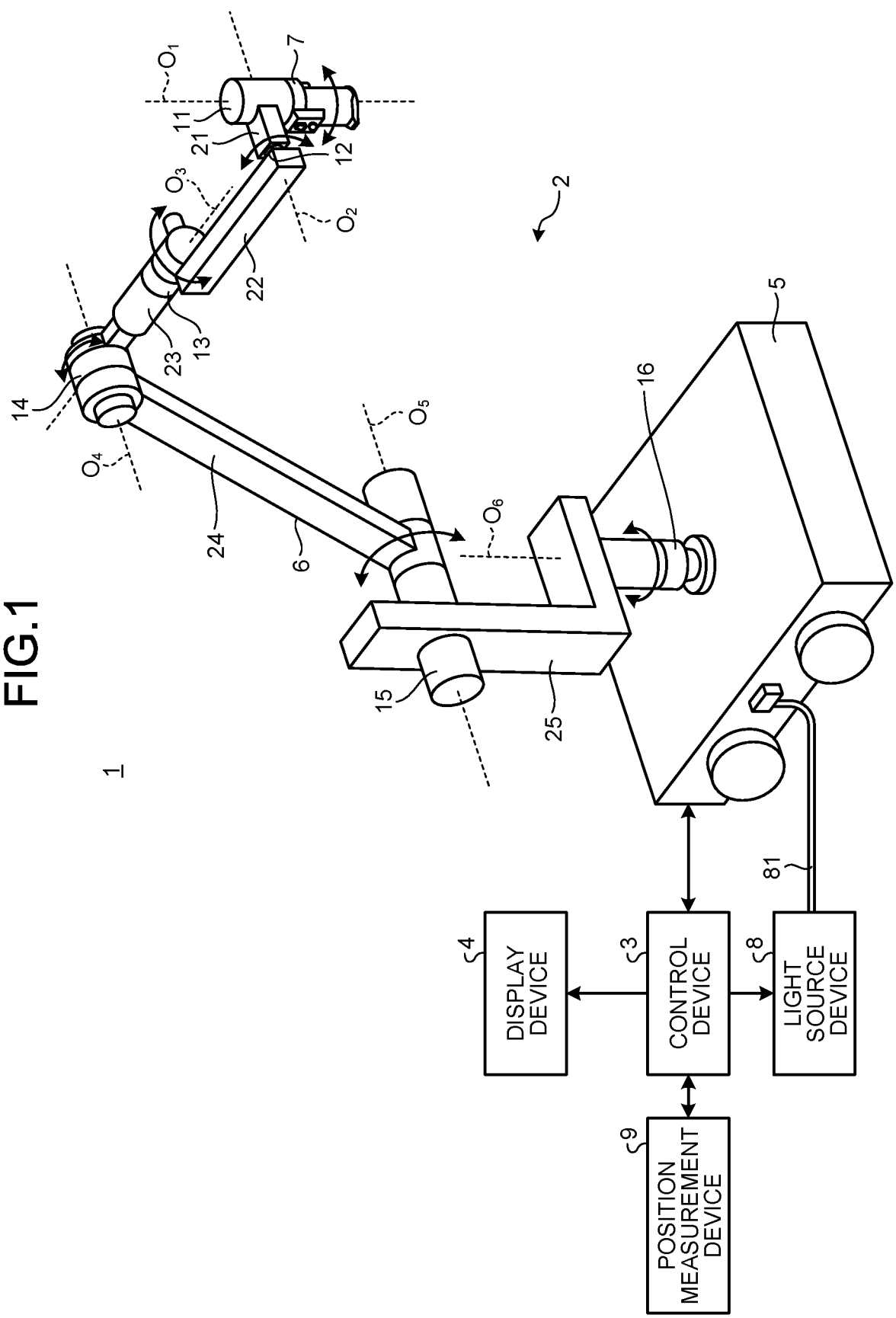
FIG. 1 is a perspective view illustrating an appearance configuration of a medical observation system according to a first embodiment.

Hereinafter, embodiments for carrying out the present disclosure (hereinafter, referred to as embodiments) will be described with reference to the accompanying drawings. Note that the drawings are merely schematic, and portions for which the relationships between dimensions and the proportions are different among drawings may be included in the drawings.

First Embodiment

FIG. 1 is a diagram illustrating a configuration of a medical observation system according to a first embodiment. A medical observation system 1 illustrated in FIG. 1 includes a microscope device 2 having a function as a microscope that magnifies and captures an image of a minute structure of an object to be observed, a control device 3 which comprehensively controls operation of the medical observation system 1, a display device 4 which displays the image captured by the microscope device 2, and a position measurement device 9 which measures a three-dimensional position of a microscope unit of the microscope device 2. The microscope device 2 and the control device 3 constitute a medical observation apparatus. Further, the display device 4 and the position measurement device 9 constitute a navigation apparatus.

The microscope device 2 includes a base unit 5 that is movable on a floor surface, a support unit 6 supported by the base unit 5, and a columnar microscope unit 7 provided at a distal end of the support unit 6 and magnifying and capturing an image of a minute part of the object to be observed. Further, the microscope device 2 is connected to a light source device 8 which supplies illumination light to the microscope device 2 via a light guide 81 implemented by an optical fiber or the like. The light source device 8 emits illumination light under the control of the control device 3.

In the microscope device 2, a cable group including, for example, a transmission cable including a signal line (coaxial cable) for signal transmission between the control device 3 and the microscope unit 7, or a light guide cable for guiding illumination light from the light source device 8 to the microscope unit 7 is arranged from the base unit 5 to the microscope unit 7. The cable group is arranged along the support unit 6.

The support unit 6 includes a first joint unit 11, a first arm unit 21, a second joint unit 12, a second arm unit 22, a third joint unit 13, a third arm unit 23, a fourth joint unit 14, a fourth arm unit 24, a fifth joint unit 15, a fifth arm unit 25, and a sixth joint unit 16. The support unit 6 includes four sets each including two arm units and a joint unit that rotatably connects one (distal end side) of the two arm units to the other one (proximal end side). Specifically, these four sets are (the first arm unit 21, the second joint unit 12, and the second arm unit 22), (the second arm unit 22, the third joint unit 13, and the third arm unit 23), (the third arm unit 23, the fourth joint unit 14, and the fourth arm unit 24), and (the fourth arm unit 24, the fifth joint unit 15, and the fifth arm unit 25).

The first joint unit 11 has a distal end rotatably holding the microscope unit 7 and a proximal end held by the first arm unit 21 in a state of being fixed to a distal end portion of the first arm unit 21. The first joint unit 11 has a circular cylindrical shape and holds the microscope unit 7 so as to be rotatable around a first axis $O_1$ which is a central axis in a height direction. The first arm unit 21 has a shape extending from a side surface of the first joint unit 11 in a direction orthogonal to the first axis $O_1$.

The second joint unit 12 has a distal end rotatably holding the first arm unit 21 and a proximal end held by the second arm unit 22 in a state of being fixed to a distal end portion of the second arm unit 22. The second joint unit 12 has a circular cylindrical shape and holds the first arm unit 21 so as to be rotatable around a second axis $O_2$ which is a central axis in the height direction and is orthogonal to the first axis $O_1$. The second arm unit 22 has a substantial "L"-letter shape and an end portion of a vertical line portion of the "L"-letter shape is connected to the second joint unit 12.

The third joint unit 13 has a distal end rotatably holding a horizontal line portion of the "L"-letter shape of the second arm unit 22, and a proximal end held by the third arm unit 23 in a state of being fixed to a distal end portion of the third arm unit 23. The third joint unit 13 has a circular cylindrical shape and holds the second arm unit 22 so as to be rotatable around a third axis $O_3$ which is a central axis in the height direction, is orthogonal to the second axis $O_2$, and is parallel to a direction in which the second arm unit 22 extends. The distal end of the third arm unit 23 has a circular cylindrical shape and a hole that penetrates in a direction orthogonal to a height direction of the circular cylindrical distal end is formed at a proximal end of the third arm unit 23. The third joint unit 13 is rotatably held by the fourth joint unit 14 through this hole.

The fourth joint unit 14 has a distal end rotatably holding the third arm unit 23 and a proximal end held by the fourth arm unit 24 in a state of being fixed to the fourth arm unit 24. The fourth joint unit 14 has a circular cylindrical shape and holds the third arm unit 23 so as to be rotatable around a fourth axis $O_4$ which is a central axis in the height direction and is orthogonal to the third axis $O_3$.

The fifth joint unit 15 has a distal end rotatably holding the fourth arm unit 24 and a proximal end fixedly attached to the fifth arm unit 25. The fifth joint unit 15 has a circular cylindrical shape and holds the fourth arm unit 24 so as to be rotatable around a fifth axis $O_5$ which is a central axis in the height direction and is parallel to the fourth axis $O_4$. The fifth arm unit 25 includes a portion with an "L"-letter shape and a rod-shaped portion extending downward from a horizontal line portion of the "L"-letter shape. The proximal end of the fifth joint unit 15 is attached to an end portion of a vertical line portion of the "L"-letter shape of the fifth arm unit 25.

The sixth joint unit 16 has a distal end rotatably holding the fifth arm unit 25 and a proximal end fixedly attached to an upper surface of the base unit 5. The sixth joint unit 16 has a circular cylindrical shape and holds the fifth arm unit 25 so as to be rotatable around a sixth axis $O_6$ which is a central axis in the height direction and is orthogonal to the fifth axis $O_5$. A proximal end portion of the rod-shaped portion of the fifth arm unit 25 is attached to the distal end of the sixth joint unit 16.

The support unit 6 having the above-described configuration implements movement with a total of 6 degrees of freedom, that is, 3 degrees of freedom of translation and 3 degrees of freedom of rotation, for the microscope unit 7.

The first joint unit 11 to the sixth joint unit 16 have electromagnetic brakes that prohibit rotation of the microscope unit 7 and the first arm unit 21 to the fifth arm unit 25, respectively. Each electromagnetic brake is released in a state in which an arm operation switch (described later) provided in the microscope unit 7 is pressed, and allows rotation of the microscope unit 7 and the first arm unit 21 to the fifth arm unit 25. Note that an air brake may be applied instead of the electromagnetic brake.

In addition to the electromagnetic brake described above, an encoder and an actuator may be mounted on each joint unit. For example, in a case where the encoder is provided in the first joint unit 11, the encoder detects a rotation angle on the first axis $O_1$. The actuator is implemented by an electric motor such as a servo motor, and is driven according to a control of the control device 3 to cause rotation at the joint unit by a predetermined angle. The rotation angle at the joint unit is set by the control device 3 based on a rotation angle on each rotation axis (the first axis $O_1$ to the sixth axis $O_6$), for example, as a value necessary for moving the microscope unit 7. As such, the joint unit provided with an active driving mechanism such as an actuator constitutes a rotation shaft that rotates actively according to a control of the driving of the actuator.

In the microscope unit 7, an imaging unit that magnifies and captures an image of the object to be observed, the arm operation switch that receives an operation input for releasing the electromagnetic brakes of the first joint unit 11 to the sixth joint unit 16 to allow the rotation of each joint unit, and a cross lever that may change a magnification and a focal length to the object to be observed in the imaging unit are provided in a casing having a circular cylindrical shape. While the user presses the arm operation switch, the electromagnetic brakes of the first joint unit 11 to the sixth joint unit 16 are released. The configuration of the imaging unit will be described later.

The control device 3 receives an imaging signal output from the microscope device 2, and generates display image data by performing predetermined signal processing on the imaging signal. Note that the control device 3 may be installed inside the base unit 5 and integrated with the microscope device 2.

Figure 2:
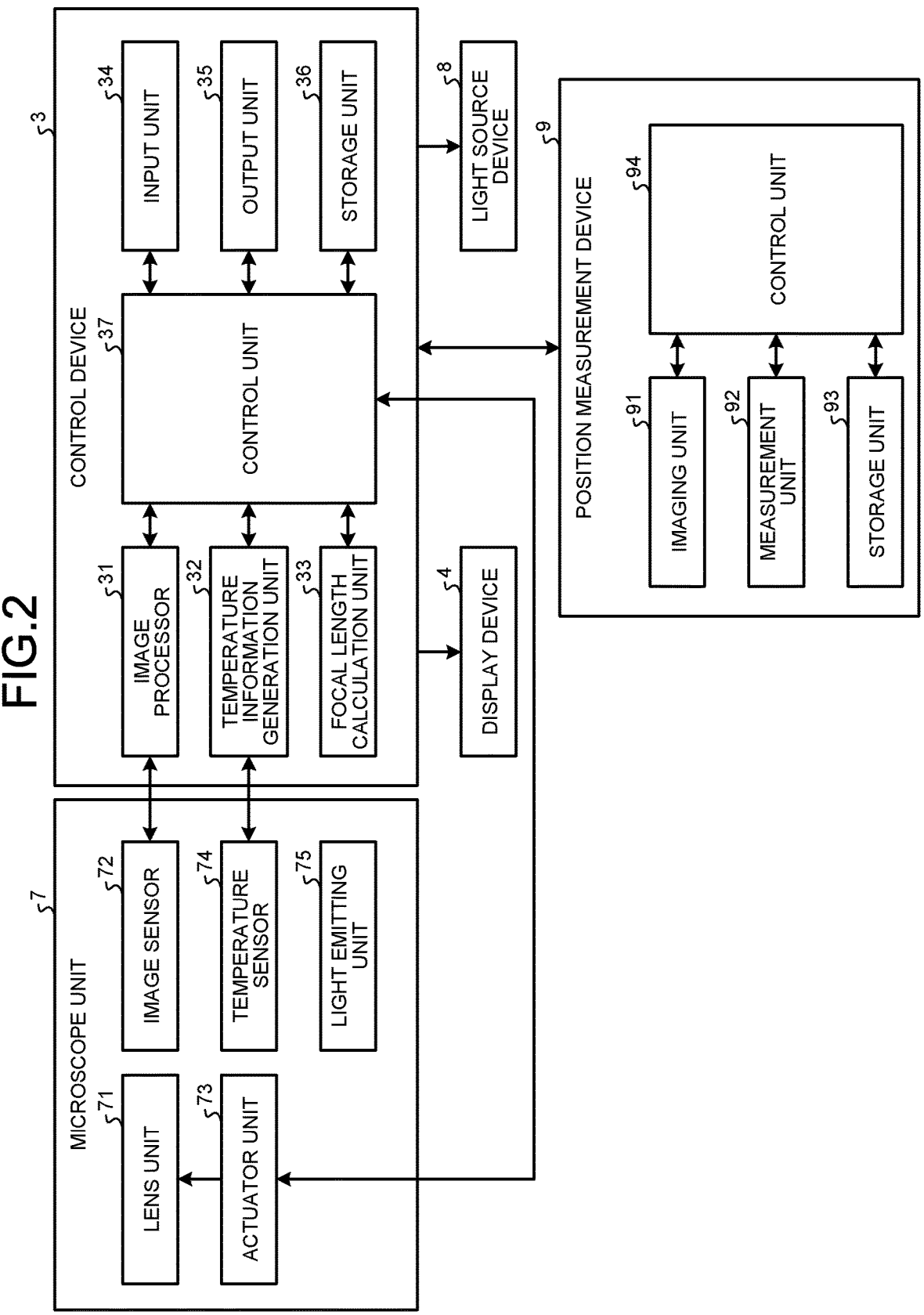
FIG. 2 is a block diagram illustrating a configuration of a control device of the medical observation system according to the first embodiment.

FIG. 2 is a block diagram illustrating a configuration of the control device of the medical observation system according to the first embodiment. The control device 3 includes an image processor 31, a temperature information generation unit 32, a focal length calculation unit 33, an input unit 34, an output unit 35, a storage unit 36, and a control unit 37. Note that, for example, a power supply unit (not illustrated) which generates a power supply voltage for driving the microscope device 2 and the control device 3, supplies the power supply voltage to each component of the control device 3, and supplies the power supply voltage to the microscope device 2 via the transmission cable may be provided in the control device 3.

The image processor 31 performs signal processing such as noise removal and A/D conversion as necessary on the imaging signal output from the microscope unit 7. The image processor 31 generates a display image signal to be displayed on the display device 4 based on the imaging signal after the signal processing. The image processor 31 performs predetermined signal processing on the imaging signal to generate a display image signal including a subject image. Here, the image processor 31 performs various known image processing such as detection processing, interpolation processing, color correction processing, color enhancement processing, and contour enhancement processing. The image processor 31 outputs the generated image signal to the display device 4.

Further, the image processor 31 may include an autofocus (AF) processor which outputs a predetermined AF evaluation value for each frame based on an input imaging signal of a frame, and an AF calculation unit which performs AF calculation processing such as selection of a frame or a focus lens position that is most suitable as a focusing position based on the AF evaluation value for each frame output from the AF processor.

The temperature information generation unit 32 obtains a detection signal from a temperature sensor 74 provided in the microscope unit 7 and generates temperature information. The temperature information generation unit 32 extracts a detection value from an analog/digital detection signal obtained from the temperature sensor, and generates temperature information based on the detection value. The temperature information is output as an environmental temperature around the lens in a lens unit 71.

The focal length calculation unit 33 calculates an actual focal length based on the temperature information generated by the temperature information generation unit 32 and information on a lens position in the lens unit 71 that is obtained from an actuator unit 73 of the microscope unit 7. A method for calculating the focal length will be described later.

The input unit 34 is implemented by a user interface such as a keyboard, a mouse, or a touch panel, and receives an input of various information.

The output unit 35 is implemented by a speaker, a printer, a display, or the like, and outputs various information.

The storage unit 36 is implemented by a semiconductor memory such as a flash memory or a dynamic random access memory (DRAM), and communication information data (for example, communication format information), a voice recognition table in which a frequency of voice and feature data are associated with each other, a processing table in which a voice recognition result and a processing content are associated with each other, and the like are recorded in the storage unit 36. Note that various programs executed by the control unit 37 may be recorded in the storage unit 36.

The control unit 37 performs a driving control of each component including the control device 3 and the microscope unit 7, an input and output control of information with respect to each component, and the like. The control unit 37 generates a control signal by referring to the communication information data (for example, communication format information) recorded in the storage unit 36, and transmits the generated control signal to the microscope device 2.

Note that the control unit 37 generates a synchronization signal and a clock for the microscope unit 7 and the control device 3. A synchronization signal (for example, a synchronization signal for instructing an image capturing timing) or a clock (for example, a clock for serial communication) for the microscope unit 7 is transmitted to the microscope unit 7 through a line (not illustrated), and the microscope unit 7 is driven based on the synchronization signal and clock.

The image processor 31, the temperature information generation unit 32, the focal length calculation unit 33, and the control unit 37 described above are each implemented by a general-purpose processor such as a central processing unit (CPU) including an internal memory (not illustrated) in which a program is recorded, or a dedicated processor such as various types of arithmetic circuits that performs a specific function, such as an application specific integrated circuit (ASIC).

Alternatively, the image processor 31, the temperature information generation unit 32, the focal length calculation unit 33, and the control unit 37 described above may each implemented by a field programmable gate array (FPGA, not illustrated) which is a kind of programmable integrated circuit. Note that, in a case of the FPGA, a memory storing configuration data may be provided, and the FPGA, which is a programmable integrated circuit, may be configured based on the configuration data read from the memory.

Next, a configuration of the imaging unit of the microscope unit 7 will be described. As illustrated in FIG. 2, the microscope unit 7 includes the lens unit 71, an image sensor 72, the actuator unit 73, a temperature sensor 74, and a light emitting unit 75.

The lens unit 71 is constituted by a plurality of lenses, and forms a subject image that has passed through the lens unit 71 on an imaging surface of the image sensor 72. At least some of the plurality of lenses are movable along an optical axis.

Figure 3:
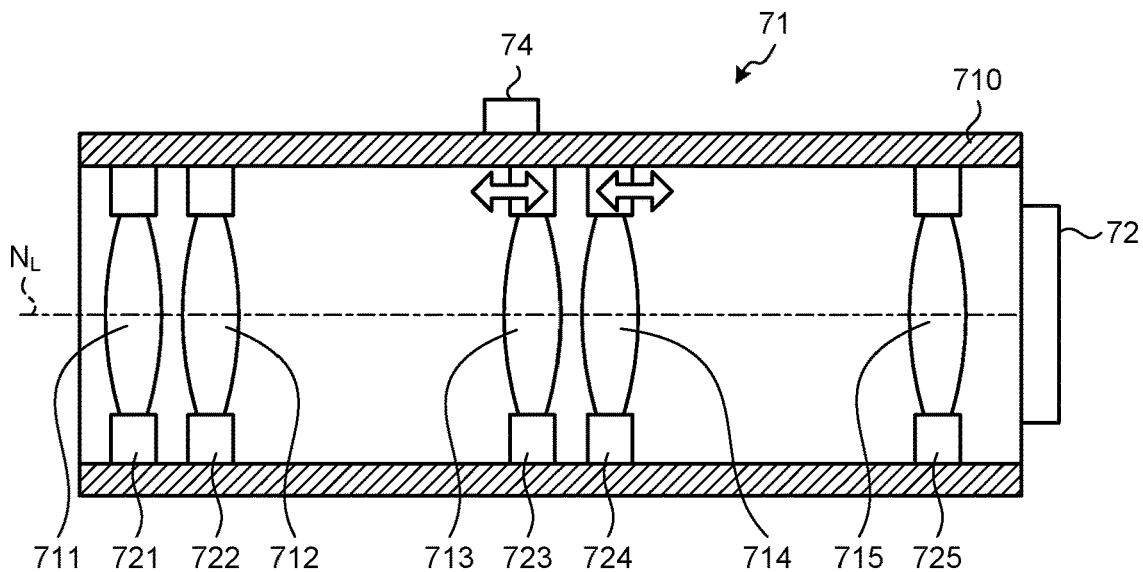
FIG. 3 is a partial cross-sectional view illustrating a configuration of a main part of an imaging unit in a microscope unit according to the first embodiment.

FIG. 3 is a partial cross-sectional view illustrating a configuration of a main part of the imaging unit in the microscope unit according to the first embodiment. In the lens unit 71, a first lens 711 to a fifth lens 715 are provided along an optical axis $N_L$. The first lens 711 to the fifth lens 715 constitute an optical system in the imaging unit. According to the first embodiment, the first lens 711 functions as an objective lens. Further, the fifth lens 715 functions as a tube lens that forms an image on the imaging surface of the image sensor 72. The first lens 711 to the fifth lens 715 are held by a first holding unit 721 to a fifth holding unit 725, respectively. Further, the first holding unit 721 to the fifth holding unit 725 are held inside a cylindrical casing 710. Among these, the third holding unit 723 and the fourth holding unit 724 are movable in a direction of the optical axis $N_L$ by the actuator unit 73.

Further, the casing 710 holds the image sensor 72 so that the image sensor 72 matches an image forming position of the fifth lens 715.

The image sensor 72 captures an image of a subject under the control of the control device 3. The image sensor 72 receives the subject image formed by the lens unit 71 and converts the subject image into an electrical signal (imaging signal). The image sensor 72 is implemented by a CCD image sensor or a complementary metal oxide semiconductor (CMOS) image sensor. In a case where the image sensor 72 is a CCD image sensor, for example, a signal processor (not illustrated) which performs signal processing (A/D conversion or the like) on the electrical signal (analog signal) obtained from the image sensor and outputs an imaging signal is packaged in a sensor chip or the like. In a case where the image sensor 72 is a CMOS image sensor, for example, a signal processor (not illustrated) which performs signal processing (A/D conversion or the like) on an electrical signal (analog signal) obtained by conversion from light to an electrical signal and outputs an imaging signal is included in the image sensor. The microscope unit 7 outputs the generated imaging signal to the image processor 31.

The actuator unit 73 performs optical zoom processing for changing an angle of view or focus processing for changing a focal position by moving one or a plurality of lenses based on a control signal from the control device 3. According to the first embodiment, at least one of the third holding unit 723 that holds the third lens 713 and the fourth holding unit 724 that holds the fourth lens 714 is moved in the direction of the optical axis $N_L$. The actuator unit 73 is constituted by an actuator or an encoder that moves the lens.

Further, the actuator unit 73 outputs lens position information to the control device 3.

The temperature sensor 74 is constituted by a known temperature detector such as a thermistor. The temperature sensor 74 digitizes, for example, an electromotive force or a resistance that changes with temperature. The temperature sensor 74 outputs a digitized detection result to the temperature information generation unit 32.

The temperature sensor 74 is provided on an outer surface of the casing 710. According to the first embodiment, the temperature sensor 74 is provided in a movement range of the third lens 713 in the direction of the optical axis $N_L$ and on an outer circumferential surface of the casing 710. Note that the temperature sensor 74 may be provided on an inner wall of the casing 710 as long as the temperature sensor 74 does not affect the movement of the lens.

The light emitting unit 75 is fixed at a predetermined position on a side surface of the microscope unit 7 and is constituted by three light emitting diodes (LEDs) that emit infrared light, respectively. The infrared light emitted from the light emitting unit 75 is used when the position measurement device 9 measures a three-dimensional position of the microscope device 2.

The display device 4 receives, from the control device 3, a three-dimensional image data generated by the control device 3, and displays a three-dimensional image corresponding to the three-dimensional image data. Such a display device 4 includes a display panel formed of liquid crystal or organic electro luminescence (EL).

Note that an output device which outputs information using a speaker, a printer, or the like may be provided in addition to the display device 4.

The position measurement device 9 is a device that measures a three-dimensional position of the microscope unit 7. The position measurement device 9 includes an imaging unit 91, a measurement unit 92, a storage unit 93, and a control unit 94.

The imaging unit 91 is constituted by an image sensor such as a CCD image sensor or a CMOS image sensor, and detects infrared rays radiated by the light emitting unit 75 of the microscope unit 7.

The measurement unit 92 measures the three-dimensional position of the microscope unit 7 of the microscope device 2 using the infrared rays acquired by the imaging unit 91.

The storage unit 93 stores various programs executed by the position measurement device 9, and temporarily stores data that are being calculated by the position measurement device 9. The storage unit 93 is constituted by a read only memory (ROM), a random access memory (RAM), or the like.

The control unit 94 controls an operation of the position measurement device 9. The control unit 94 is constituted by one or a plurality of processors such as a CPU, an FPGA, and an ASIC together with the measurement unit 92.

Next, an overview of an operation performed using the medical observation system 1 having the above-described configuration will be described. When an operator who is a user performs an operation on the head of a patient who is an object to be observed, the operator grips the microscope unit 7, moves the microscope unit 7 to a desired position in a state of keeping the arm operation switch of the microscope unit 7 pressed, determines an imaging visual field of the microscope unit 7, and then removes his/her finger from the arm operation switch, while visually observing an image displayed on the display device 4. Thereby, the electromagnetic brakes are operated in the first joint unit 11 to the sixth joint unit 16, and the imaging visual field of the microscope unit 7 is fixed.

Thereafter, the operator performs adjustment of the magnification and the focal length to the object to be observed, and the like.

Figure 4:
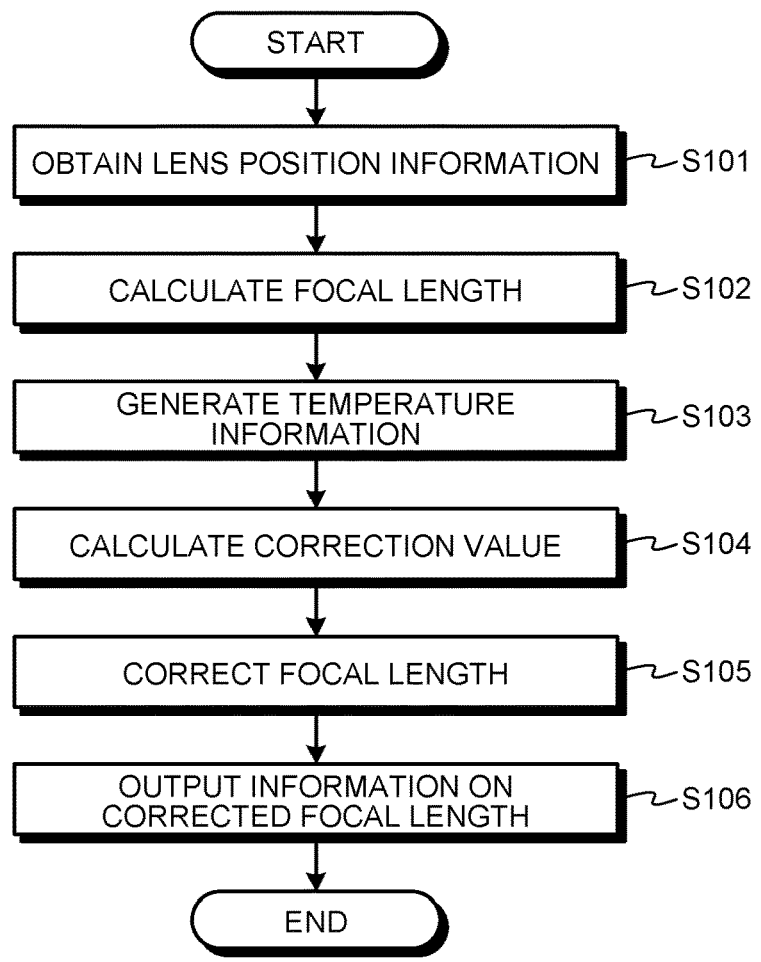
FIG. 4 is a flowchart illustrating focal length calculation processing performed by the control device of the medical observation system according to the first embodiment.

Next, focal length calculation processing performed by the control device 3 will be described with reference to FIG. 4. FIG. 4 is a flowchart illustrating focal length calculation processing performed by the control device of the medical observation system according to the first embodiment. When a focal length calculation instruction is input, the control unit 37 starts focal length calculation processing.

The control unit 37 obtains lens position information (Step S101). The control unit 37 obtains the lens position information on a lens position from the actuator unit 73. The focal length calculation unit 33 calculates a focal length (uncorrected focal length) based on the information on a lens position in the lens unit 71 obtained from the actuator unit 73 (Step S102). The uncorrected focal length corresponds to a first focal length.

Further, the temperature information generation unit 32 obtains a detection signal from the temperature sensor 74 and generates temperature information (Step S103).

The focal length calculation unit 33 calculates a correction value based on the temperature information generated in Step S103 (Step S104). The focal length calculation unit 33 calculates the correction value by using the following Equation (1).

$$\text{Correction value} = (X-T) \times Q \qquad (1)$$

Here, $Q=B(Y)$.

Figures 5, 6:
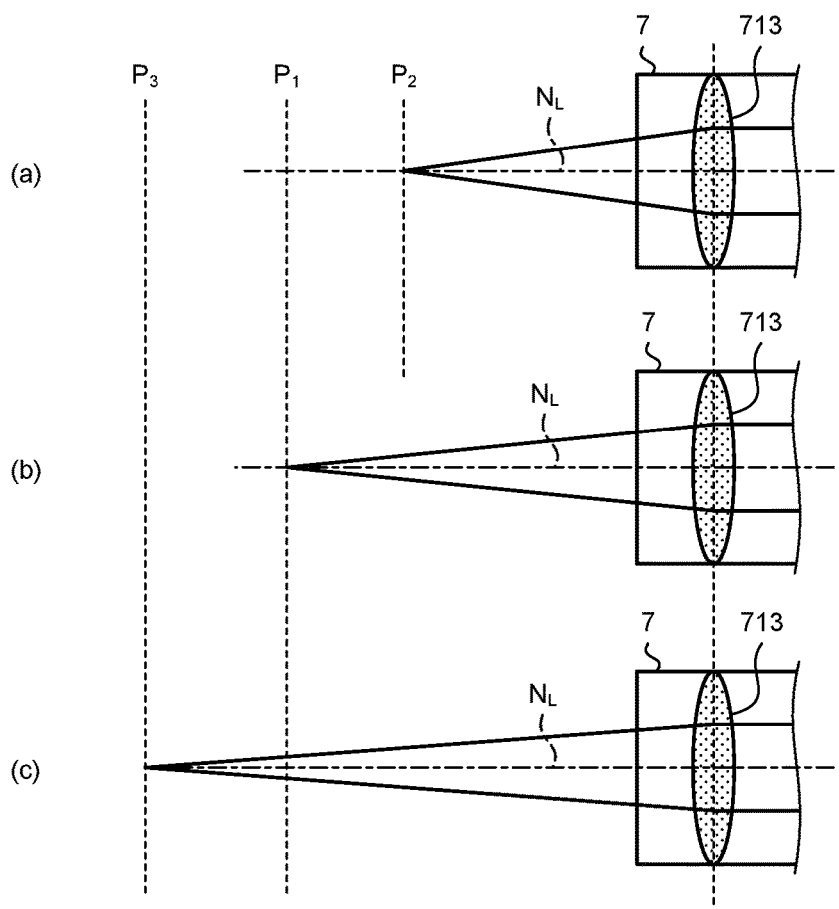
FIG. 5 is a diagram for describing a focal length change depending on a temperature.
FIG. 6 is a diagram for describing an example of a correction result for each temperature.

X: Obtained temperature (° C.) of the lens unit 71
T: Reference temperature (° C.)
Q: Focal length change amount per unit temperature
B( ): Change amount conversion formula
Y: Uncorrected focal length FIG. 5 is a diagram for describing a focal length change depending on a temperature. (a) of FIG. 5 is a diagram illustrating a focal length when the temperature (environmental temperature) of the lens unit 71 is 10° C. (b) of FIG. 5 is a diagram illustrating a focal length when the temperature (environmental temperature) of the lens unit 71 is 25° C. (c) of FIG. 5 is a diagram illustrating a focal length when the temperature (environmental temperature) of the lens unit 71 is 40° C. In FIG. 5, only the third lens 713 to be driven is illustrated, and the other lenses are not illustrated.

Further, in the first embodiment, the reference temperature is 25° C.

Even when all the lenses including the third lens 713 are arranged at the same positions, the focal position changes due to a change in lens characteristics depending on a temperature. In FIG. 5, a focal position $P_2$ when the environmental temperature is 10° C. and a focal position $P_3$ when the environmental temperature is 40° C. are different from a focal position $P_1$ when the environmental temperature is 25° C. As such, even in a case where the lens position is not changed, the focal position changes depending on the environmental temperature. Therefore, the actual focal length also changes depending on the environmental temperature. Specifically, the focal length when the environmental temperature is 10° C. is smaller and the focal length when the environmental temperature is 40° C. is larger than the focal length when the environmental temperature is the reference temperature (25° C.)

The focal length calculation unit 33 calculates the above-described amount of the focal length change depending on a temperature as a correction value for the focal position calculated based on the lens position, and corrects the focal position (Step S105).

FIG. 6 is a diagram for describing an example of a correction result for each temperature. For example, in a case where the focal length when the environmental temperature is 25° C. (reference temperature) is 500 mm (WD500), if a correction value when the environmental temperature is 10° C. is calculated to be −10 mm and a correction value when the environmental temperature is 40° C. is calculated to be +10 mm (a correction value when the environmental temperature is 25° C. is 0, because 25° C. is the reference temperature) according to Equation (1), an actual focal length (corrected focal length) when the environmental temperature is 10° C. is 490 mm (WD490), and an actual focal length (corrected focal length) when the environmental temperature is 40° C. is 510 mm (WD510). On the other hand, in a case of not performing the correction, the focal length (corrected focal length) is 500 mm (WD500) regardless of the environmental temperature. The corrected focal length corresponds to a second focal length.

Here, WD indicates a working distance.

Once the corrected focal length is calculated by the focal length calculation unit 33, the control unit 37 outputs information on the calculated corrected focal length to the display device 4 or the navigation apparatus (Step S106). As a result, a value closer to the actual focal length is output.

For example, the control unit 94 of the position measurement device 9 calculates a focal position in an image based on the position of the microscope unit 7 measured by the position measurement device 9 and a direction of the optical axis of the microscope unit 7 at the position of the microscope unit 7, and generates a display image by applying information on a result of the calculation and the like to an image captured by the microscope unit 7. The focal position in the image captured by the microscope unit 7 is displayed on the display device 4 together with the corrected focal length. The focal position in the image is indicated by, for example, an arrow.

In addition, a display image in which information on the corrected focal length is superimposed on the image captured by the microscope unit 7 may be displayed on the display device 4.

According to the first embodiment described above, since the focal length is corrected based on the uncorrected focal length obtained based on the lens position and the detected environmental temperature in the lens unit 71, the focal length calculation unit 33 may obtain a focal length corresponding to a use environmental temperature.

Further, according to the first embodiment, since the temperature sensor 74 is arranged in the vicinity of the lens (here, the third lens 713) to be driven, the temperature of the lens that causes the change in the focal length is used for the correction of the focal length, such that the focal length may be accurately corrected.

In the first embodiment described above, an example in which the focal length calculation unit 33 calculates the correction value based on the uncorrected focal length and the temperature information has been described, but the correction value may also be calculated based on optical characteristic values such as a thermal expansion coefficient, a refractive index, and a temperature characteristic value of the lens, in addition to the uncorrected focal length and the temperature information. For these optical characteristic values, for example, values measured at the reference temperature (here, 25° C.) are used as calibration values (values at the reference temperature) at the time of product shipment in a factory.

Modified Example of First Embodiment

Figures 7, 8:
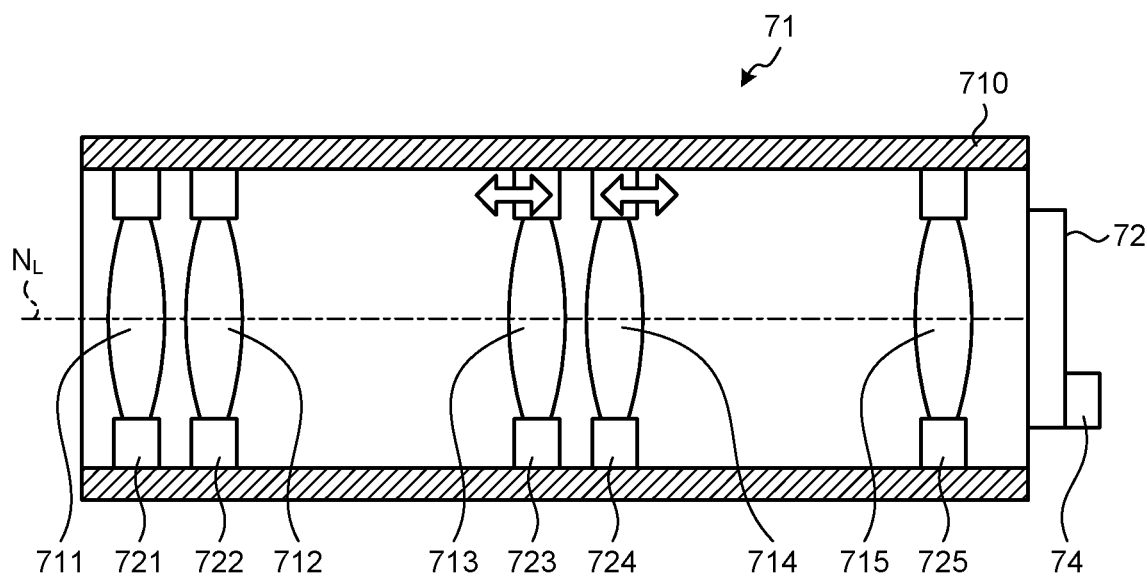
FIG. 7 is a diagram for describing an example of a table for calculating a correction value used at the time of performing focal length calculation processing according to a modified example of the first embodiment.
FIG. 8 is a partial cross-sectional view illustrating a configuration of an optical unit of a microscope unit of a medical observation system according to a second embodiment.

Next, a modified example of the first embodiment will be described with reference to FIG. 7. FIG. 7 is a diagram for describing an example of a table for calculating a correction value used at the time of performing focal length calculation processing according to a modified example of the first embodiment. Since a medical observation system according to the modified example has the same configuration as that of the medical observation system 1 according to the first embodiment described above, a description thereof is omitted. In the first embodiment described above, an example in which the correction value is calculated by using an equation (Equation (1)) has been described. However, in the modified example, the correction value is obtained by using a preset correction value output table. Each value in the correction value output table is set in consideration of optical characteristic values such as a thermal expansion coefficient, a refractive index, and a temperature characteristic value of the lens, in addition to the uncorrected focal length and the temperature information.

In the modified example, a flow of focal length calculation processing is the same as that in the flowchart illustrated in FIG. 4. Here, in Step S104, the focal length calculation unit 33 acquires the correction value by using the correction value output table illustrated in FIG. 7 instead of calculating the correction value by using Equation (1). The focal length calculation unit 33 outputs a correction value for each temperature separately for a case where the uncorrected focal length is 200 mm (WD200) or more and less than 400 mm (WD400), and a case where the uncorrected focal length is 400 mm (WD400) or more and 600 mm (WD600) or less, with reference to the correction value output table.

The subsequent processing is the same as that in FIG. 4.

In the modified example described above, similarly to the first embodiment described above, since the focal length is corrected based on the uncorrected focal length obtained based on the lens position and the detected environmental temperature in the lens unit 71, the focal length calculation unit 33 may obtain an accurate focal length corresponding to a use environmental temperature.

Second Embodiment

Next, a second embodiment will be described with reference to FIG. 8. FIG. 8 is a partial cross-sectional view illustrating a configuration of an optical unit of a microscope unit of a medical observation system according to the second embodiment. The medical observation system according to the second embodiment has the same configuration as that of the medical observation system 1 of the first embodiment described above except that an arrangement position of the temperature sensor 74 is changed, and thus a description of a configuration of each component is omitted. Hereinafter, a difference from the first embodiment will be described.

The temperature sensor 74 is provided on a surface of the image sensor 72 that is opposite to a surface facing the casing 710. Similar to the first embodiment, the temperature sensor 74 outputs a digitized detection result to the temperature information generation unit 32.

In the second embodiment, a flow of focal length calculation processing is the same as that in the flowchart illustrated in FIG. 4. For calculation of the correction value, Equation (1) or the correction value output table (see FIG. 7) may be used.

In the second embodiment described above, similarly to the first embodiment described above, since the focal length is corrected based on the uncorrected focal length obtained based on the lens position and the detected environmental temperature in the lens unit 71, the focal length calculation unit 33 may obtain an accurate focal length corresponding to a use environmental temperature. Further, according to the second embodiment, since the temperature sensor 74 is arranged in the vicinity of the image sensor 72, a temperature of a member that causes the change in the lens temperature is used for the correction of the focal length, such that the focal length may be accurately corrected.

Third Embodiment

Figure 9:
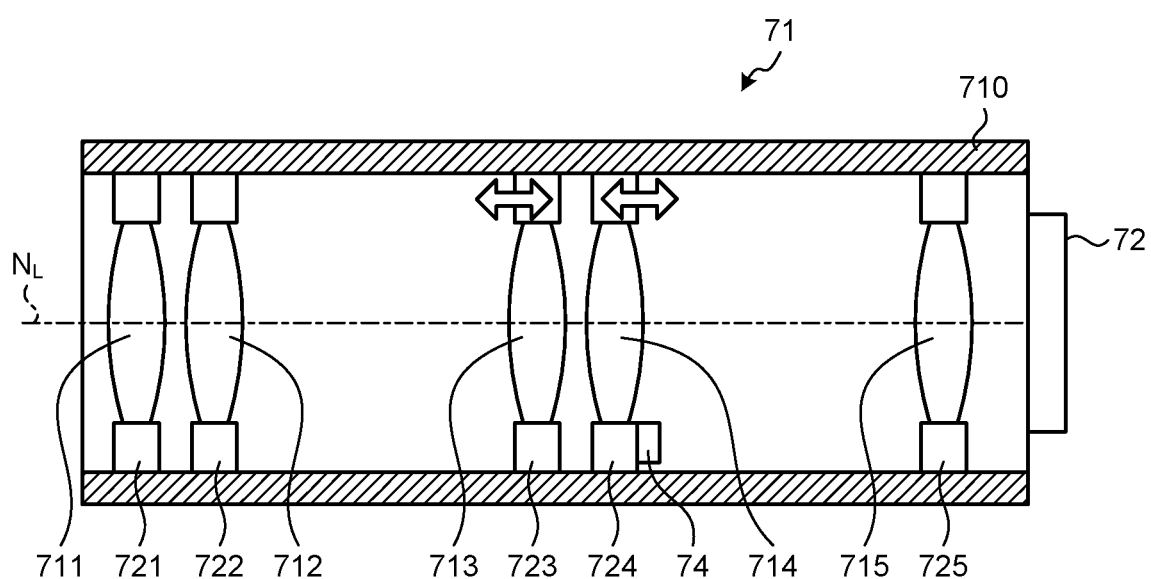
FIG. 9 is a partial cross-sectional view illustrating a configuration of an optical unit of a microscope unit of a medical observation system according to a third embodiment.

Next, a third embodiment will be described with reference to FIG. 9. FIG. 9 is a partial cross-sectional view illustrating a configuration of an optical unit of a microscope unit of a medical observation system according to the third embodiment. The medical observation system according to the third embodiment has the same configuration as that of the medical observation system 1 of the first embodiment described above except that an arrangement position of the temperature sensor 74 is changed, and thus a description of a configuration of each component is omitted. Hereinafter, a difference from the first embodiment will be described.

The temperature sensor 74 is provided on any one of the plurality of lenses. According to the third embodiment, the temperature sensor 74 is provided on a lens having a refractive index highly dependent on temperature, specifically, a lens (here, the fourth lens 714) having the highest thermal expansion coefficient. Note that the temperature sensor 74 is provided outside a light passing region of the lens.

Similar to the first embodiment, the temperature sensor 74 outputs a digitized detection result to the temperature information generation unit 32.

In the third embodiment, a flow of focal length calculation processing is the same as that in the flowchart illustrated in FIG. 4. For calculation of the correction value, Equation (1) or the correction value output table (see FIG. 7) may be used.

In the third embodiment described above, similarly to the first embodiment described above, since the focal length is corrected based on the uncorrected focal length obtained based on the lens position and the detected environmental temperature in the lens unit 71, the focal length calculation unit 33 may obtain an accurate focal length corresponding to a use environmental temperature.

Further, according to the third embodiment, since the temperature sensor 74 is arranged directly on a lens having a refractive index highly dependent on temperature, the temperature of the lens that directly affects an error of the focal length is used for the correction of the focal length, such that the focal length may be accurately corrected.

Hereinabove, the embodiments for carrying out the present disclosure have been described, but the present disclosure should not be limited only to the embodiments described above. For example, it is sufficient that the support unit 6 includes at least one set including two arm units and a joint unit that rotatably connects one of the two arm units to the other one.

Note that although the configuration in which the focal length may be changed by moving the lens has been described in the first to third embodiments as an example, a configuration in which the optical system has a fixed focal length and the focal length is corrected based on a detection result obtained by the temperature sensor may also be possible.

Further, although the configuration in which one temperature sensor is provided has been described in the first to third embodiments as an example, a configuration in which a plurality of temperature sensors are provided and an average value, a mode value, or the like is used as temperature information to obtain a correction value may also be possible.

Moreover, the microscope device may be arranged so as to be suspended from a ceiling of a place where the microscope device is installed.

As described above, the present disclosure may include various embodiments and the like without departing from the technical idea described in the claims.

As described above, the medical observation apparatus and the medical observation system according to the present disclosure are useful for obtaining a focal length corresponding to a use environmental temperature.

According to the present disclosure, it is possible to obtain a focal length corresponding to a use environmental temperature.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation apparatus comprising:
   an optical structure including at least one lens;
   an image sensor configured to capture an image formed by the optical structure;
   a temperature sensor configured to detect an environmental temperature of the optical structure;
   a memory that stores data including first focal length correction values according to temperature and second focal length correction values according to temperature, the first focal length correction values being for a first lens within a first range of uncorrected focal length, and the second focal length correction values being for a second lens within a second range of uncorrected focal length; and
   circuitry configured to
      generate temperature information based on a detection result of the temperature sensor,
      calculate a focal length of the at least one lens based on a lens position of the at least one lens,
      identify whether the at least one lens belong to the first lens or the second lens based on the calculated focal length of the at least one lens, and calculate a second focal length obtained by correcting the calculated focal length of the at least one lens based on the data, by identifying a correction value corresponding to the temperature information from either the first focal length correction values or the second focal length correction values depending on whether the at least one lens has been identified as belonging to the first lens or the second lens.

2. The medical observation apparatus according to claim 1, further comprising an actuator configured to drive the at least one lens of the optical structure,
wherein the circuitry is configured to calculate the first focal length based on lens position information obtained from the actuator.

3. The medical observation apparatus according to claim 1, wherein the circuitry is configured to correct the first focal length by using the temperature information, the first focal length, and optical characteristic values of the optical structure.

4. The medical observation apparatus according to claim 1, further comprising a casing configured to hold the optical structure,
wherein the temperature sensor is provided on the casing.

5. The medical observation apparatus according to claim 1, wherein the temperature sensor is provided on the image sensor.

6. The medical observation apparatus according to claim 1, wherein the temperature sensor is provided on the lens included in the optical structure.

7. The medical observation apparatus according to claim 1, wherein information on the calculated second focal length is output to an external navigation apparatus.

8. A medical observation system comprising:
a medical observation apparatus including
an optical structure including at least one lens,
an image sensor configured to capture an image formed by the optical structure,
a temperature sensor configured to detect an environmental temperature of the optical structure,
a memory that stores data including first focal length correction values according to temperature and second focal length correction values according to temperature, the first focal length correction values being for a first lens within a first range of uncorrected focal length, and the second focal length correction values being for a second lens within a second range of uncorrected focal length, and
circuitry configured to
generate temperature information based on a detection result of the temperature sensor,
calculate a focal length of the at least one lens based on a lens position of the at least one lens,
identify whether the at least one lens belong to the first lens or the second lens based on the calculated focal length of the at least one lens, and
calculate a second focal length obtained by correcting the calculated focal length of the at least one lens based on the data, by identifying a correction value corresponding to the temperature information from either the first focal length correction values or the second focal length correction values depending on whether the at least one lens has been identified as belonging to the first lens or the second lens;
a position measurement device configured to measure a three-dimensional position of a casing on which the image sensor is provided; and
a display panel configured to display information on the three-dimensional position of the casing measured by the position measurement device, together with the image captured by the image sensor.

* * * * *